(12) United States Patent
Paratian et al.

(10) Patent No.: US 12,012,378 B2
(45) Date of Patent: Jun. 18, 2024

(54) METHOD FOR SYNTHESIZING 2-BROMOGLUTARIC ACID DIESTERS

(71) Applicant: GUERBET, Villepinte (FR)

(72) Inventors: Jean-Michel Paratian, La Rochelle (FR); Martine Cerf, Breuil-Magné (FR)

(73) Assignee: GUERBET, Villepinte (FR)

( * ) Notice: Subject to any disclaimer, the term of this patent is extended or adjusted under 35 U.S.C. 154(b) by 0 days.

(21) Appl. No.: 18/011,683

(22) PCT Filed: Jul. 16, 2021

(86) PCT No.: PCT/EP2021/070022
§ 371 (c)(1),
(2) Date: Dec. 20, 2022

(87) PCT Pub. No.: WO2022/013440
PCT Pub. Date: Jan. 20, 2022

(65) Prior Publication Data
US 2023/0303477 A1    Sep. 28, 2023

(30) Foreign Application Priority Data

Jul. 16, 2020    (EP) .................................... 20305823

(51) Int. Cl.
| C07C 69/63 | (2006.01) |
| C07C 67/08 | (2006.01) |
| C07C 67/307 | (2006.01) |
| C07C 67/54 | (2006.01) |
| C07D 307/33 | (2006.01) |

(52) U.S. Cl.
CPC .............. *C07C 69/63* (2013.01); *C07C 67/08* (2013.01); *C07C 67/307* (2013.01); *C07C 67/54* (2013.01); *C07D 307/33* (2013.01)

(58) Field of Classification Search
CPC ....... C07C 69/63; C07C 67/08; C07C 67/307; C07C 67/54; C07C 69/62; C07C 69/675; C07D 307/33
See application file for complete search history.

(56) References Cited

U.S. PATENT DOCUMENTS 6,440,956 B1 *   8/2002   Port ...................... C07D 471/08
                                                                    534/10
2020/0376145 A1 * 12/2020 Napolitano .......... A61K 49/106

FOREIGN PATENT DOCUMENTS

| CN | 101233097 B | | 6/2011 |
| CS | 209266 | * | 5/1983 |
| CS | 209266 B1 | | 5/1983 |
| EP | 1 931 673 B1 | | 8/2012 |
| GB | 577877 A | | 6/1946 |
| WO | WO2007/017018 A1 | | 2/2007 |

OTHER PUBLICATIONS

Kielar et al. (Large Relaxivity Enhancement of Paramagnetic Lipid Nanoparticles by Restricting the Local Motions of the GdIII Chelates, J. of Amer. Chem. Soc., pp. 7836-7837, Published May 2010) (Year: 2010).*
Kielar et al. Supporting Information, pp. 1-25 (Year: 2010).*
Teichmann (Reactions with Brominated Dicarboxylic Acids, I. On the Synthesis of Aliphatic alpha-Bromodicarboxylic Acids, Acta Chim. Hung. Tomus, 41, pp. 331-336, Published 1964) (Year: 1964).*
Teichmann Translation 20 pages (Year: 1964).*
Carniato et al., "A Chemical Strategy for the Relaxivity Enhancement of GdIII Chelates Anchored on Mesoporous Silica Nanoparticles," Chemistry—A European Journal, vol. 16, 2010, pp. 10727-10734.

* cited by examiner

*Primary Examiner* — Yevgeny Valenrod
*Assistant Examiner* — Blaine G Doletski
(74) *Attorney, Agent, or Firm* — Birch, Stewart, Kolasch & Birch, LLP

(57) ABSTRACT

The present invention relates to a process for preparing the 2-bromoglutaric acid diester of formula (I) below:

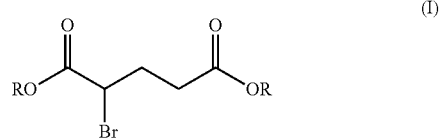

comprising the formation of the 2-hydroxyglutaric acid diester of formula (II)

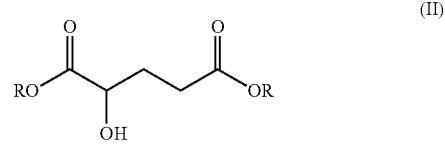

by reaction of butyrolactone acid of formula (BA)

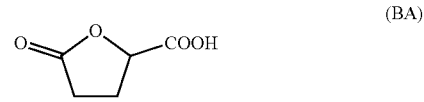

with the alcohol of formula ROH, in the presence of an acid such as sulfuric acid; and bromination of the 2-hydroxyglutaric acid diester of formula (II), by sparging with gaseous hydrobromic acid.
The present invention also relates to a 2-bromoglutaric acid diester of formula (I), having a degree of purity determined by HPLC analysis of greater than or equal to 90%.

20 Claims, 1 Drawing Sheet

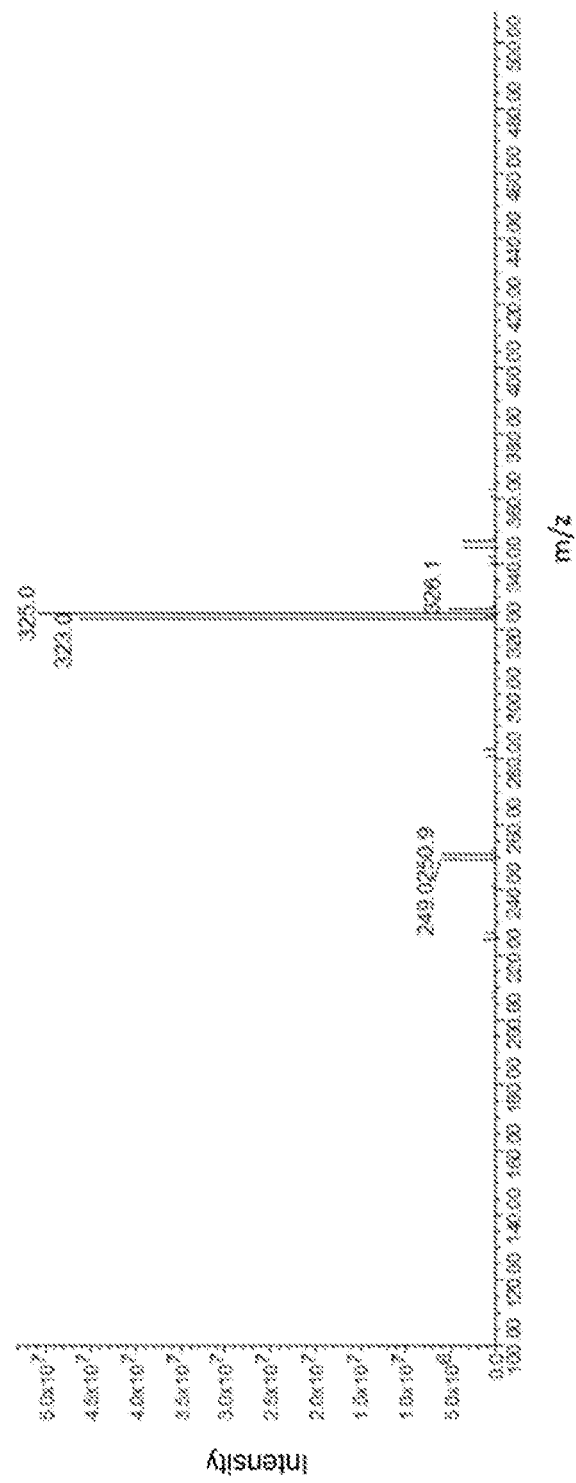

METHOD FOR SYNTHESIZING 2-BROMOGLUTARIC ACID DIESTERS

The present invention relates to a novel process for preparing 2-bromoglutaric acid diesters.

α-Haloglutaric acids and esters thereof are useful basic building blocks in organic synthesis, which make it possible to incorporate, into a complex molecule, an α-glutaric acid fragment via a simple nucleophilic substitution reaction.

EP 1 931 673 describes novel gadolinium complexes derived from PCTA, which have applications as contrast agents in the field of medical imaging. The side chains of some of these complexes, notably of gadopiclenol, include an α-glutaric acid fragment. The synthesis of gadopiclenol, in the form of a mixture of all its stereoisomers, as described in EP 1 931 673, involves the alkylation of pyclene with diethyl 2-bromoglutarate, resulting in an intermediate hexaester, which is then hydrolyzed to give the corresponding hexaacid, which is then complexed with a source of gadolinium. The gadopiclenol prepared according to the process described in EP 1 931 673 is finally obtained by reacting the gadolinium hexaacid complex with 3-amino-1,2-propanediol.

The inventors thus sought an alternative to EBG, which would be more stable than it, while at the same time being sufficiently reactive to achieve the synthesis of gadopiclenol, for example. Thus, chloro derivatives of glutaric acid, which meet the criterion of improved stability relative to EBG, do not constitute a satisfactory option, insofar as they do not have sufficient reactivity. Iodo derivatives are, for their part, more reactive than their bromo analogs, but are also more unstable. The investigations conducted by the inventors enabled them to select di-($C_3$-$C_6$)-alkyl 2-bromoglutarate compounds as an alternative to EBG, in particular in the synthesis of gadopiclenol. However, the corresponding commercial products do not have a high enough degree of purity to be used in the preparation of a pharmaceutical product intended for human administration, such as gadopiclenol.

It is thus necessary to develop a novel process for preparing di-($C_3$-$C_6$)-alkyl 2-bromoglutarate compounds, which enables them to be obtained with a sufficient degree of purity, and which can be performed efficiently on an industrial scale.

Now, the synthesis of 2-bromoglutaric acid diesters is very sparingly described in the literature. Patent CS 209266 B1, granted in 1983, is, to the inventors' knowledge, the

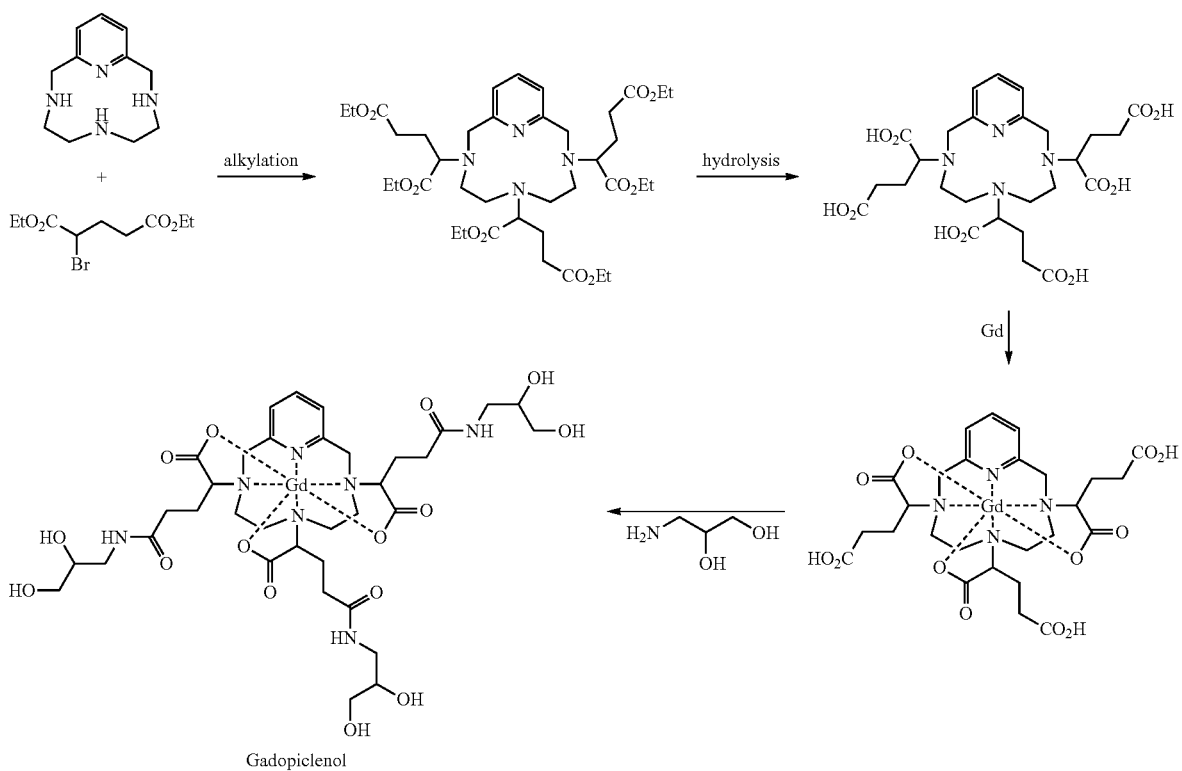

Synthesis of gadopiclenol

Gadopiclenol

Diethyl 2-bromoglutarate (referred to as EBG hereinbelow) is a relatively unstable compound, which degrades over time, under the effect of the temperature or in the presence of water. More precisely, this particular α-haloglutaric ester has a tendency to become hydrolyzed or to cyclize and thus to lose its bromine atom. Attempts to purify commercial EBG, or to develop novel synthetic routes for obtaining it with improved purity, and thus preventing its degradation, have been unfruitful.

only document that mentions the preparation of these compounds. It relates in general to a process for preparing an α-haloglutaric acid or an alkyl diester thereof of formula R'$O_2$CCH$_2$CH$_2$CH(X)CO$_2$R", in which R' and R" are ($C_1$-$C_5$)alkyl groups and X corresponds to a bromine or chlorine atom, the emphasis however being clearly placed on the preparation of the chloro derivatives. Said derivatives are obtained by chlorination of the glutaric acid diester in the presence of an antimony-based catalyst. Although said document asserts that the method described makes it possible to perform monochlorination in the α position with better selectivity than in the processes of the prior art, the fact remains that appreciable amounts of β-chloro or α-dichloro and trichloro derivatives are formed, the selectivity with respect to the α-monochloro product ranging between 63.16% and 86.1% depending on the nature of the antimony-based catalyst, the degree of conversion of the starting ester itself oscillating between 86.10% and 98.9%. It should be noted that the conditions for which the degree of conversion of the starting material is the highest allow the α-monochloro product to be obtained with a selectivity of only 79%. Another major drawback of this process is, moreover, the use of antimony, which is extremely toxic.

The present invention thus relates to a process for preparing the 2-bromoglutaric acid diester of formula (I) below:

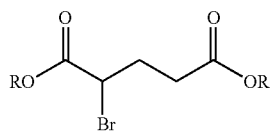
(I)

in which R represents a (C$_3$-C$_6$)alkyl group,
comprising the following steps:
(b) formation of the 2-hydroxyglutaric acid diester of formula (II)

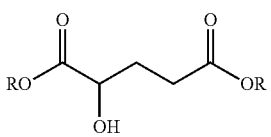
(II)

by reaction of butyrolactone acid of formula (BA)

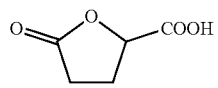
(BA)

with the alcohol of formula ROH, in the presence of an acid such as sulfuric acid; and
(c) bromination of the 2-hydroxyglutaric acid diester of formula (II), by sparging with gaseous hydrobromic acid, leading to the 2-bromoglutaric acid diester of formula (I).

For the purposes of the present invention, the term "(C$_3$-C$_6$)alkyl group" means a linear or branched, saturated hydrocarbon-based chain including 3 to 6 carbon atoms. By way of example, mention may be made of propyl, isopropyl, n-butyl, isobutyl, sec-butyl, tert-butyl, pentyl or hexyl groups, in particular the n-butyl group, also referred to as butyl.

The butyrolactone acid of formula (BA) is also referred to as carboxy-γ-butyrolactone.

According to a preferred embodiment, R corresponds to a butyl group, and the process according to the invention makes it possible to prepare dibutyl 2-bromoglutarate of formula (BBG), also known as dibutyl 2-bromo-1,5-pentanedioate (CAS No: 104867-13-2).

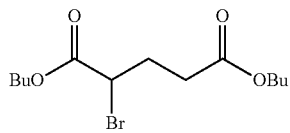
(BBG)

In a particular embodiment, the process according to the invention comprises a first step (a) of forming butyrolactone acid of formula (BA) by reacting L-glutamic acid with sodium nitrite in aqueous solution.

Step (a)

This first step consists in forming butyrolactone acid (BA) from L-glutamic acid, a commonly available starting material, according to a reaction that is well known to those skilled in the art.

L-Glutamic acid is introduced into water, the ratio of the mass of water used to the mass of L-glutamic acid introduced typically being greater than 1, notably greater than 1.5, typically equal to 2. The density of water being equal to 1 g/mL, in the continuation of the description, such a ratio of the mass of water (or, by analogy, of any other solvent or solution) to the mass of a solute will be designated by the expression "volume equivalent" or its abbreviation "vol. eq.".

Preferentially, the water used in the process is water of at least the same quality as deionized water, so as to avoid the formation of impurities, such as an α-chloro impurity. In particular, it may be deionized water or water for injection (WFI).

The resulting aqueous solution is then typically heated with stirring, to a temperature advantageously between 40° C. and 70° C., in particular between 45° C. and 65° C., preferably between 50° C. and 60° C., notably at 55° C.

An aqueous sodium nitrite solution is then added gradually to the L-glutamic acid solution, preferably with stirring and while maintaining the previously established temperature.

Said aqueous sodium nitrite solution is such that the amount of water used represents, for example, between 0.8 and 5.0 vol. eq., notably between 1.0 and 3.0 vol. eq., typically 2 vol. eq. relative to the mass of sodium nitrite which it contains.

The sodium nitrite may notably be introduced into the L-glutamic acid solution in slight excess relative to the stoichiometric proportions. The ratio of the amount of material introduced as sodium nitrite to the amount of material initially introduced as L-glutamic acid is then greater than 1, but typically less than 1.5, notably less than 1.3, advantageously less than 1.2. In other words, the amount of sodium nitrite introduced is greater than 1 molar equivalent (mol. eq.), but typically less than 1.5 mol. eq., notably less than 1.3 mol. eq., advantageously less than 1.2 mol. eq., relative to the amount of L-glutamic acid initially introduced, which itself corresponds to 1 molar equivalent.

The reaction mixture comprising sodium nitrite and L-glutamic acid is then typically kept under stirring at a temperature advantageously between 40° C. and 70° C., in particular between 45° C. and 65° C., preferably between 50° C. and 60° C., notably at 55° C., for a period of time allowing the various compounds present in solution to be dissolved, typically between 2 h and 10 h, preferably between 2 h and 5 h.

It is then cooled to a temperature advantageously between 10° C. and 45° C., preferentially between 10° C. and 35° C., in particular between 15° C. and 30° C., preferably between 20° C. and 25° C., and then neutralized by addition of an acid solution, for example hydrochloric acid, preferably at 33% m/m, the amount of material introduced as hydrochloric acid then being close to, typically equal to Thus, the amount of material introduced as hydrochloric acid is greater than 1 molar equivalent (mol. eq.), but typically less than 1.5 mol. eq., notably less than 1.3 mol. eq., advantageously less than 1.2 mol. eq., relative to the amount of L-glutamic acid initially introduced.

The reaction mixture thus neutralized is then typically concentrated under vacuum, by gradually increasing the temperature, up to a value above 50° C., for example 60° C.

In the continuation of the description, the expression "under vacuum" is intended to denote a pressure of between 10 and 500 mbar, notably between 10 and 350 mbar, preferably between 10 and 150 mbar, in particular between 50 and 100 mbar, the temperature being specified, where appropriate.

As regards the vacuum concentration operation for producing crude butyrolactone acid (BA) on conclusion of step (a), this is typically performed at a pressure of less than 100 mbar by gradually increasing the temperature until it reaches 60° C.

Preferentially, steps (a) and (b) are performed according to a one-pot embodiment, i.e. without an intermediate step of isolation or purification.

Step (b)

Step (b) is directed toward forming the 2-hydroxyglutaric acid diester of formula (II)

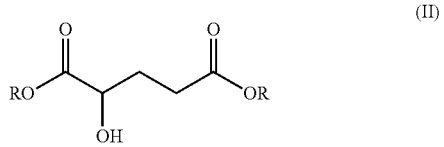

by reaction of butyrolactone acid of formula (BA) with the alcohol of formula ROH.

In a preferred embodiment, butyrolactone acid (BA) is obtained from step (a) described previously, and has not been purified before being employed in step (b).

During this step, the opening of the lactone and the formation of the two ester functions —C(O)OR take place concomitantly or successively.

The alcohol ROH is preferably introduced in excess relative to the butyrolactone acid. Thus, the amount of ROH introduced is preferably greater than or equal to 2 molar equivalents (mol. eq.), notably greater than or equal to 4 mol. eq., advantageously between 2 and 10 mol. eq., in particular between 4 and 10 mol. eq., typically equal to 5 mol. eq., relative to the amount of butyrolactone acid initially introduced. It should be noted that when the butyrolactone acid is obtained from step (a), the amount of ROH introduced is expressed relative to the amount of L-glutamic acid initially introduced, the number of mol. eq. indicated remaining unchanged.

In a preferred embodiment, step (b) is performed in the presence of the acetate of formula $CH_3COOR$. The amount of acetate introduced is then typically between 0.1 and 0.7 mol. eq., notably between 0.2 and 0.5 mol. eq., advantageously between 0.3 and 0.4 mol. eq., relative to the amount of alcohol ROH introduced.

The formation of the two ester functions —C(O)OR, which takes place during step (b), may advantageously be performed by acid catalysis. Thus, step (b) is preferably performed in the presence of a catalytic amount of acid, for example sulfuric acid. Under such conditions, the lactone is liable to open up to form the 2-hydroxyglutaric acid of formula (HG), the esterification of its carboxylic acid functions with the alcohol ROH subsequently taking place.

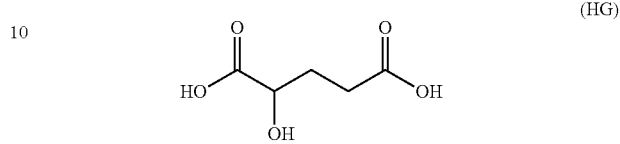

Thus, step (b) of the process according to the invention also comprises the formation of the 2-hydroxyglutaric acid diester of formula (II) by reaction of 2-hydroxyglutaric acid of formula (HG) with the alcohol of formula ROH.

Conversely, butyrolactone acid (BA) can undergo a first esterification reaction before ring opening, to form the following esterified lactone of formula (BR) below.

Thus, step (b) of the process according to the invention also comprises the formation of the 2-hydroxyglutaric acid diester of formula (II) by reaction of the esterified lactone of formula (BR) with the alcohol of formula ROH.

As will emerge clearly to those skilled in the art, the process according to the invention may be performed using as starting material for step (b) 2-hydroxyglutaric acid of formula (HG) or the esterified lactone of formula (BR) as an alternative to butyrolactone acid (BA).

In a preferred embodiment, the water present in the reaction mixture of step (b), typically formed in situ, is removed by vacuum distillation, until a reaction medium having a mass fraction of water of less than 2% w/w, preferably less than 1.5% w/w, advantageously less than 0.8% w/w, is obtained.

Said reaction mixture of step (b) also notably comprises butyrolactone acid of formula (BA), the alcohol of formula ROH, and advantageously acetate of formula $CH_3COOR$.

Advantageously, the vacuum distillation is a vacuum azeotropic distillation.

For the purposes of the present invention, the term "vacuum azeotropic distillation" means the distillation of an azeotropic mixture performed at a pressure of between 10 and 500 mbar, notably between 10 and 350 mbar, preferably between 10 and 150 mbar, in particular between 50 and 100 mbar, which makes it possible to remove one of the constituents of the azeotropic mixture.

In the present case, the azeotropic mixture is a water/ROH/$CH_3COOR$ ternary azeotropic mixture, and the vacuum azeotropic distillation allows the water to be removed from the mixture.

According to a preferred embodiment, R corresponds to a butyl group (Bu), and the azeotropic mixture is a water/BuOH/$CH_3COOBu$ ternary mixture. This azeotrope is characterized by a boiling point of between 85° C. and 95° C., more precisely between 87° C. and 93° C., even more precisely between 89° C. and 91.5° C., typically equal to 89.4° C., at atmospheric pressure.

The vacuum azeotropic distillation of the water/BuOH/CH$_3$COOBu ternary mixture is typically performed at a pressure of between 10 and 500 mbar, notably between 10 and 350 mbar, preferably between 10 and 150 mbar, in particular between 50 and 125 mbar, and at a temperature of between 20° C. and 100° C., notably between 30° C. and 70° C.

In a preferred embodiment, on conclusion of step (b), the reaction medium is cooled to a temperature below 15° C., notably below 10° C., in particular between 0° C. and 5° C.

This cooling step typically takes place after the vacuum distillation, which is preferably a vacuum azeotropic distillation of the reaction mixture, as described previously.

In a preferred embodiment, on conclusion of step (b), the cooled reaction medium is left to separate by settling after addition of water so as to obtain the formation of an organic phase and a separate aqueous phase, said aqueous phase then being removed.

This operation is advantageously performed several times, typically between 2 and 5 times, in particular 3 times.

The amount of water added represents, for example, between 0.1 and 2 vol. eq. relative to the mass of butyrolactone acid initially used. It should be noted that when the butyrolactone acid comes from step (a), the amount of water added is expressed relative to the mass of L-glutamic acid initially introduced, the number of vol. eq. remaining unchanged.

When the water addition/separation by settling operation is performed several times, the amount of water added for the first cycle is typically between 1 and 2 vol. eq., and the amount of water added for the following cycles is typically between 0.1 and 0.5 vol. eq.

The reaction medium obtained on conclusion of step (b), preferably the organic phase recovered after the water addition/separation by settling operation(s), typically comprises the 2-hydroxyglutaric acid diester of formula (II) as the majority species, and also the esterified lactone of formula (BR), in solution in the alcohol ROH, advantageously as a mixture with the acetate of formula CH$_3$COOR.

According to a preferred embodiment, R corresponds to a butyl group (Bu), and the reaction medium obtained on conclusion of step (b), preferably the organic phase recovered after the water addition/separation by settling operation(s), typically comprises dibutyl 2-hydroxyglutarate of formula (BHG) as the majority species, and also the butyrolactone acid butyl ester of formula (BBE), in solution in butanol BuOH, advantageously as a mixture with butyl acetate CH$_3$COOBu.

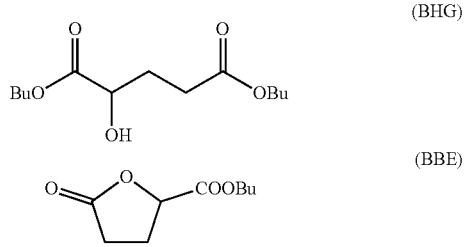

In a preferred embodiment, the reaction medium obtained on conclusion of step (b), preferably the organic phase recovered after the water addition/separation by settling operation(s), is then dehydrated by vacuum distillation, at a pressure of between 10 and 500 mbar, notably between 10 and 350 mbar, preferably between 10 and 150 mbar, in particular between 50 and 100 mbar.

Advantageously, this is a vacuum azeotropic distillation of the water/ROH/CH$_3$COOR mixture, in particular water/BuOH/CH$_3$COOBu, and vacuum azeotropic distillation allows the water to be removed from the mixture.

In a preferred embodiment, the reaction medium obtained on conclusion of step (b), preferably the organic phase recovered after the water addition/separation by settling operation(s), advantageously dehydrated by vacuum distillation, at a pressure of between 10 and 500 mbar, in particular between 10 and 350 mbar, preferably between 10 and 150 mbar, in particular between 50 and 100 mbar, is then concentrated under vacuum before being subjected to step (c), so as to remove some of the ROH/CH$_3$COOR mixture, in particular BuOH/CH$_3$COOBu.

The amount of said mixture removed is typically between 1 and 2 vol. eq. relative to the mass of butyrolactone acid initially used or relative to the mass of L-glutamic acid initially introduced when the butyrolactone acid is obtained from step (a).

In the continuation of the description, the operations of cooling, addition of water/separation by settling, dehydration by vacuum distillation and/or concentration under vacuum described previously are considered to be an integral part of step (b) when they are performed.

Preferentially, steps (b) and (c) are performed according to a one-pot embodiment, i.e. without an intermediate step of isolation or purification.

Step (c)

Step (c) is directed toward forming the 2-bromoglutaric acid diester of formula (I) by bromination of the 2-hydroxyglutaric acid diester of formula (II) obtained in step (b).

As will emerge clearly to a person skilled in the art from the detailed description of step (b), the reaction medium obtained on conclusion of step (b) typically comprises the 2-hydroxyglutaric acid diester of formula (II) as the majority species, along with the esterified lactone of formula (BR), in solution in the alcohol ROH, advantageously as a mixture with the acetate of formula CH$_3$COOR.

Consequently, although step (c) is directed toward forming the 2-bromoglutaric acid diester of formula (I) by bromination of the 2-hydroxyglutaric acid diester of formula (II), the formation of the 2-hydroxyglutaric acid diester of formula (II) by reaction of the esterified lactone of formula (BR) with the alcohol ROH can typically continue during this step, the opening of the lactone being facilitated by the introduction of the brominating agent into the reaction medium.

Step (c) typically begins by setting the temperature of the reaction medium to a value of between 5° C. and 40° C., advantageously between 10° C. and 30° C., in particular to 20° C.

Gaseous hydrobromic acid is then gradually introduced into the reaction medium by sparging.

In a preferred embodiment, the amount of gaseous hydrobromic acid introduced is then typically between 1 and 1.5 mol. eq., notably between 1.2 and 1.3 mol. eq., relative to the amount of butyrolactone acid used in step (b) or relative to the amount of L-glutamic acid initially introduced in step (a).

In a preferred embodiment, the reaction medium obtained after introduction of the gaseous hydrobromic acid is then dehydrated by vacuum distillation, at a pressure typically between 10 and 500 mbar, notably between 10 and 350 mbar, preferably between 10 and 150 mbar, in particular between 50 and 100 mbar, for a time typically between 3 h and 8 h, advantageously between 5 h and 7 h.

Advantageously, the vacuum distillation is a vacuum azeotropic distillation of the water/ROH/CH$_3$COOR mixture, in particular water/BuOH/CH$_3$COOBu. Such a vacuum azeotropic distillation allows the water to be removed from the mixture.

The temperature of the reaction medium is then typically restored to a value of between 5° C. and 40° C., advantageously between 10° C. and 30° C., in particular to 20° C.

In a preferred embodiment, the cycle of operations described previously, namely setting the temperature of the reaction medium to a value of between 5° C. and 40° C., introducing gaseous hydrobromic acid in an amount typically between 1 and 1.5 mol. eq. relative to the amount of butyrolactone acid used in step (b) or relative to the amount of L-glutamic acid initially introduced in step (a), vacuum distillation for a period of between 3 h and 8 h so as to remove water from the reaction medium, and restoring the temperature of the reaction medium to a value of between 5° C. and 40° C., is repeated from 3 to 8 times, preferably from 4 to 6 times.

The reaction medium obtained on conclusion of step (c) typically comprises the 2-bromoglutaric acid diester of formula (I) in solution in the alcohol ROH, advantageously as a mixture with the acetate of formula CH$_3$COOR.

According to a preferred embodiment, R corresponds to a butyl group and the reaction medium obtained on conclusion of step (c) typically comprises dibutyl 2-bromoglutarate of formula (BBG) in solution in butanol BuOH, advantageously as a mixture with butyl acetate CH$_3$COOBu.

Alternatively, the hydrobromic acid can be formed in situ during the azeotropic distillation. In this alternative, a bromine salt, typically NaBr or KBr, is introduced into the reaction medium in place of the gaseous hydrobromic acid, and a strong acid, such as concentrated sulfuric acid (>96%), is then added.

A person skilled in the art will know how to adapt the subsequent treatment steps of the process accordingly, in particular so as to remove the salts present, for example sulfate salts, in the case of this alternative embodiment.

Steps (d)-(e)

In a preferred embodiment of the process according to the invention, the reaction mixture obtained on conclusion of step (c) is subjected to the following additional steps:

(d) introduction of the reaction mixture obtained on conclusion of step (c) into a basic aqueous solution, the solution obtained having a pH typically between 7.5 and 9.5;

(e) separation by settling of the solution obtained in step (d), so as to obtain the formation of an organic phase and a separate aqueous phase, said aqueous phase being then removed;

(f) concentration under vacuum of the organic phase obtained in step (e), until a temperature of between 65° C. and 75° C. is reached, followed by drying under vacuum;

(g) optionally, filtration, and recovery of the 2-bromoglutaric acid diester of formula (I).

In an alternative embodiment, steps (d) and (e) are not performed and step (f) is performed directly on the reaction mixture obtained on conclusion of step (c), and is optionally followed by a filtration step (g).

Step (d) may notably be performed by adding the reaction mixture obtained on conclusion of step (c) to an aqueous solution of bicarbonate ion, also called hydrogen carbonate, the amounts of potassium or sodium bicarbonate and water employed being able to be determined by a person skilled in the art so as to obtain, on conclusion of step (d), a solution having a pH typically between 7.5 and 9.5, in particular between 8 and 9, and to be able to perform separation between an aqueous and an organic phase during step (e).

The organic phase obtained in step (e) or the reaction mixture obtained on conclusion of step (c) is then concentrated under vacuum in step (f), at a pressure typically between 10 and 500 mbar, notably between 10 and 350 mbar, preferably between 10 and 150 mbar, in particular between 50 and 100 mbar, until a temperature above 50° C. is reached, in particular above 60° C., for example 70° C., so as to remove some of the ROH/CH$_3$COOR mixture, and then dried under vacuum, at a pressure typically between 10 and 350 mbar, preferably between 50 and 150 mbar, in particular between 50 and 100 mbar, until a temperature above 50° C. is reached, in particular above 60° C., for example 70° C.

This step may be followed by a filtration step (g), which may be performed using any method that is well known to those skilled in the art.

The process according to the invention makes it possible to obtain the 2-bromoglutaric acid diester of formula (I) in a yield of greater than 85%, advantageously greater than 90%, and a degree of purity, determined by HPLC analysis, of greater than or equal to 90%, in particular greater than or equal to 93%, typically greater than or equal to 95%, preferably greater than or equal to 97%, notably greater than or equal to 98%, advantageously greater than or equal to 99%.

According to a preferred embodiment, R corresponds to a butyl group, and the process according to the invention makes it possible to prepare dibutyl 2-bromoglutarate of formula (BBG) in a yield and with a degree of purity as stated previously.

The present invention thus further relates to a 2-bromoglutaric acid diester of formula (I) below:

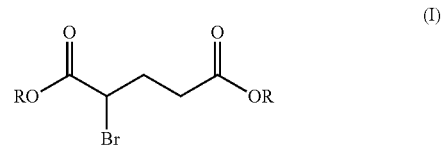

in which R represents a (C$_3$-C$_6$)alkyl group, preferably a butyl group, having a degree of purity, determined by HPLC analysis, of greater than or equal to 90%, in particular greater than or equal to 93%, typically greater than or equal to 95%, preferably greater than or equal to 97%, notably greater than or equal to 98%, advantageously greater than or equal to 99%.

Racemization Step

The 2-bromoglutaric acid diester of formula (I) may be obtained with a variable enantiomeric excess. If it is not racemic, it is possible to racemize it in an additional racemization step using a bromine salt, such as LiBr or tetrabutylammonium bromide, according to methods that are well known to those skilled in the art.

FIGURES

The FIGURE shows the mass spectrum of BBG.

EXAMPLES

The following abbreviations are used:
BBG: dibutyl 2-bromoglutarate
Bu: butyl
ee: enantiomeric excess
HPLC: High Performance Liquid Chromatography
NMR: nuclear magnetic resonance
TBAB: tetrabutylammonium bromide I. Synthesis of dibutyl 2-bromoglutarate I.1. Protocol 147.1 g (1 mol) of L-glutamic acid are dissolved in 294 g of water. This solution is heated to 55° C.±5° C. 76 g (1.1 mol) of sodium nitrite dissolved in 152 g of water are slowly added. Contact is maintained for at least 2 hours at 55° C.±5° C. until dissolution is complete, and the solution is then cooled to 20-25° C. After neutralization with about 122 g (1.1 mol) of 33% hydrochloric acid, the medium is concentrated under vacuum (<100 mbar) by gradually increasing the temperature to 60° C.

The butyrolactone acid obtained is esterified with 370 g (5 mol) of butanol in the presence of 206 g of butyl acetate and 1.47 g (0.015 mol) of sulfuric acid under azeotropic distillation and under vacuum. The reaction medium is then cooled to 0-5° C. and taken up in 221 g of water. The lower aqueous phase is removed and the organic phase washed twice more with 30 g of water. The organic phase obtained contains a mixture of butyl hydroxyglutarate/butyl ester of butyrolactone (HPLC s/s: 90/10). The mixture is dehydrated by azeotropic distillation under 50-100 mbar and then concentrated by removing the equivalent of 195 g of solvent.

The bromination is performed by performing the following operations five times in succession: sparging with 100 g (1.2 mol) of hydrobromic acid at 20±10° C., azeotropic distillation under vacuum for at least 5 hours. The reaction medium is washed with an aqueous solution of 6 g of potassium hydrogen carbonate dissolved in about 60 g of water. The aqueous phase is discarded and the organic phase is washed with water and then concentrated under vacuum until a temperature of about 70° C. is reached. BBG is obtained in a yield of 90% and a purity of 97.1% s/s as determined by HPLC.

I.2. Characterization of BBG

Boiling point 115-120° C./0.2-0.3 mmHg, i.e. about 380° C. at atmospheric pressure.

NMR performed on a JEOL 500 MHz machine:
$^1$H NMR (CDC$_3$, 400 MHz) 4.34-4.39 (m, 1H, Br—CH—COO), 4.16-4.22 (m, 2H, Br—CH—COOCH$_2$), 4.06-4.11 (m, 2H, CH$_2$—COOCH$_2$), 2.50-2.59 (m, 2H, OOC—CH$_2$—CH$_2$—CHBr), 2.25-2.43 (m, 2H, OOC—CH$_2$—CH$_2$—CHBr), 1.55-1.69 (m, 4H, CH$_2$—CH$_2$—CH$_2$), 1.34-1.45 (m, 4H, CH$_3$—CH$_2$—CH$_2$), 0.92-0.96 (m, 6H, CH$_3$—CH$_2$—CH$_2$)

Mass spectrometry

The presence of bromine in the molecule was confirmed by a mass spectrum performed using a Waters QDa mass spectrometer coupled to a Waters I-Class UHPLC machine. The mass spectrum recording was performed in positive electrospray mode at a cone voltage of 10 V.

The mass spectrum obtained is shown in the FIGURE.

The doublets with a difference of 2 confirm the presence of bromine in the molecule.

The mass at 323-325 corresponds to the parent peak, and the mass at 249-251 to the loss of butoxide.

I.3. HPLC Analysis

Equipment:
HPLC machine consisting of a pumping system, an injector, a chromatography column, a UV detector and a data station.
Spherisorb ODS 2, 250×4.6 mm—5 µm column.
96% Sulfuric acid Suprapur® (Merck 1.00714 or equivalent).
Acetonitrile (HPLC gradient grade, J.T Baker reference 8143 or equivalent).
Deionized water (Elga HPLC grade, or equivalent).

Method:
Mobile phase:
Route A: 100% acetonitrile
Route B: 0.1% v/v aqueous sulfuric acid solution Preparation of the samples:
0.2 g of BBG to be analyzed is placed in a 20 mL volumetric flask, followed by a sufficient amount of acetonitrile to make 20 mL of solution.

| Analytical conditions: | |
| --- | --- |
| Column temperature | 25° C. |
| Sample temperature | Ambient |
| Flow rate | 1.0 mL/min |
| Injection volume | 20 µl |
| UV detection | 220 nm |
| Analysis time | 70 min |

| Gradient: | | |
| --- | --- | --- |
| Time | % acetonitrile | % H$_2$SO$_4$ (0.1%) |
| 0 | 1 | 99 |
| 5 | 1 | 99 |
| 20 | 60 | 40 |
| 50 | 80 | 20 |
| 60 | 80 | 20 |
| 62 | 1 | 99 |
| 70 | 1 | 99 |

II. Racemization of dibutyl 2-bromoglutarate

During the synthesis, the asymmetric carbon retains its configuration and becomes partially racemized on bromination. The BBG is typically obtained with an enantiomeric excess ranging from 50% to 80%. If the BBG obtained is not racemic, it is possible to racemize it using a bromine salt.

II.1. With LiBr

Racemization of the BBG with 1 mol % LiBr by contact for 2 hours at 60° C.

Washing of the racemic BBG with 2×2 weight equivalents of 0.1 M sodium bicarbonate solution at 25° C.

Washing with 0.5 weight equivalent of water under vacuum (pressure s 30 mbar) and temperature of the reaction medium at s 70° C.

This process was applied with 3418 g of BBG and 9.22 g of LiBr in 97.9% yield.

Chiral HPLC monitoring was performed to achieve racemization.

Equipment:
HPLC apparatus equipped with a UV detector.
Chiralpak IC—5 µm—250×4.6 mm column from Daicel.

Method:

Mobile phase: 95% heptane/5% isopropyl alcohol

Preparation of the samples:

50 mg of BBG to be analyzed are placed in a 10 mL volumetric flask, followed by a sufficient amount of heptane to make 10 mL of solution.

Analytical conditions:

HPLC in normal phase, elution of the mobile phase in isocratic mode.

| | |
|---|---|
| Flow rate | 0.7 mL/min |
| Injection volume | 10 μl |
| UV detection | 270 nm |

Calculation of the enantiomeric excess:

% ee=(peak area 1−peak area 2)/(peak area 1+peak area 2)×100

| Conditions | % peak area Enantiomer 1 | Enantiomer 2 | % enantiomeric excess |
|---|---|---|---|
| Starting material | 21.46 | 78.54 | −57.08 |
| Contact 2 h/60° C. | 48.96 | 51.04 | −2.08 |
| Contact 2 h 30/60° C. | 49.68 | 50.32 | −0.64 |

II.2. With TBAB

It was shown that racemization is also possible with TBAB under the same conditions as with LiBr, without solvent and at room temperature.

3.2 g of TBAB are added to 323 g of BBG. The medium is stirred for at least 5 hours to reach an ee<1%. The TBAB is removed by two successive washes with 150 ml of water. The BBG is concentrated under vacuum at a temperature below 70° C.

The invention claimed is:

1. A process for preparing the 2-bromoglutaric acid diester of formula (I) below:

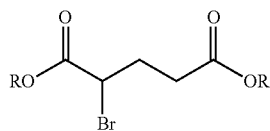

(I)

in which R represents a propyl, isopropyl, n-butyl, isobutyl, sec-butyl, pentyl or hexyl group, wherein said process comprises the following steps:

(b) forming the 2-hydroxyglutaric acid diester of formula (II)

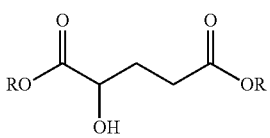

(II)

by reacting butyrolactone acid of formula (BA)

(BA)

with the alcohol of formula ROH, in the presence of an acid;

(c) brominating the 2-hydroxyglutaric acid diester of formula (II), by sparging with gaseous hydrobromic acid, thereby leading to the 2-bromoglutaric acid diester of formula (I); and wherein a degree of purity of the 2-bromoglutaric acid diester of formula (I), determined by HPLC analysis, is greater than or equal to 90%.

2. The process of claim 1, wherein step (b) is performed in the presence of the acetate of formula $CH_3COOR$.

3. The process of claim 1, wherein, during step (b), the water is removed by vacuum distillation.

4. The process of claim 1, wherein in step (b), butyrolactone acid of formula (BA) and the alcohol ROH are introduced in amounts such that the ROH/BA mole ratio is between 2 and 10.

5. The process of claim 1, wherein, on conclusion of step (b), the reaction medium is cooled to a temperature below 15° C. and is left to separate by settling after addition of water so as to obtain the formation of an organic phase and a separate aqueous phase, said aqueous phase then being removed and said organic phase being dehydrated by vacuum distillation and/or concentration under vacuum before being subjected to step (c).

6. The process of claim 1, wherein step (c) comprises the following cycle of steps:

setting the temperature of the reaction to a value of between 5° C. and 40° C., introducing gaseous hydrobromic acid in an amount of between 1 and 1.5 mol. eq. relative to the amount of butyrolactone acid (BA) used in step (b), vacuum distillation so as to remove water from the reaction, restoring the temperature of the reaction to a value of between 5° C. and 40° C.

7. The process of claim 1, wherein it comprises a first step (a) of forming butyrolactone acid of formula (BA) by reacting L-glutamic acid with sodium nitrite in aqueous solution.

8. The process of claim 1, wherein the reaction mixture obtained on conclusion of step (c) is subjected to the following additional steps:

(d) introducing the reaction mixture obtained on conclusion of step (c) into a basic aqueous solution;

(e) separating by settling the solution obtained in step (d), so as to obtain the formation of an organic phase and a separate aqueous phase, said aqueous phase being then removed;

(f) concentrating under vacuum the organic phase obtained in step (e), until a temperature of between 65° C. and 75° C. is reached, followed by drying under vacuum;

(g) optionally, filtrating; and recovering the 2-bromoglutaric acid diester of formula (I).

9. The process of claim 1, wherein the 2-bromoglutaric acid diester of formula (I) obtained on conclusion of step (c), (f) or (g) is subjected to an additional racemization step by adding a bromine salt.

10. The process of claim 1, wherein R corresponds to an n-butyl group.

11. The process of claim 3, wherein the vacuum distillation operations taking place during steps (b) and (c) are azeotropic distillations.

12. A compound of formula (I) below:

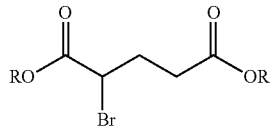

in which R represents a propyl, isopropyl, n-butyl, isobutyl, sec-butyl, pentyl or hexyl group,
with a degree of purity, determined by HPLC analysis, of greater than or equal to 90%.

13. The compound as claimed in claim 12, wherein R corresponds to an n-butyl group.

14. The compound of claim 12, wherein its degree of purity is greater than or equal to 95%.

15. The compound of claim 12, wherein its degree of purity is greater than or equal to 97%.

16. The process of claim 1, wherein the acid in step (b) is sulfuric acid.

17. The process of claim 6, wherein vacuum distillation is carried out for a time between 3 h and 8 h.

18. The process of claim 6, wherein the cycle of steps are repeated from 3 to 8 times.

19. The process of claim 8, wherein the solution obtained in step (d) has a pH typically between 7.5 and 9.5.

20. The process of claim 9, wherein the bromine salt is LiBr or tetrabutylammonium bromide.

* * * * *